United States Patent [19]

Ilvespää et al.

[11] Patent Number: 4,614,745
[45] Date of Patent: Sep. 30, 1986

[54] ANTI-ALLERGIC 3-(CARBOXYCARBONYL)AMINO BENZOTHIOPYRAN-4-ONE DERIVATIVES, COMPOSITIONS, AND METHOD OF USE THEREFOR

[75] Inventors: Atso Ilvespää, Allschwil; Georges Haas, Binningen, both of Switzerland

[73] Assignee: Ciba-Geigy Corporation, Ardsley, N.Y.

[21] Appl. No.: 722,632

[22] Filed: Apr. 12, 1985

[30] Foreign Application Priority Data

Apr. 24, 1984 [CH] Switzerland ............... 2000/84

[51] Int. Cl.$^4$ ............... C07D 335/06; A61K 31/38
[52] U.S. Cl. ............... 514/432; 549/23; 549/27
[58] Field of Search ............... 549/23, 28, 27; 514/432

[56] References Cited

U.S. PATENT DOCUMENTS

| | | | |
|---|---|---|---|
| 3,933,844 | 1/1976 | Augstein et al. | 424/269 |
| 4,013,771 | 3/1977 | Brown et al. | 424/275 |
| 4,216,155 | 8/1980 | Haas et al. | 424/283 |
| 4,288,450 | 9/1981 | Haas et al. | 424/283 |

Primary Examiner—Henry R. Jiles
Assistant Examiner—J. G. Mullins
Attorney, Agent, or Firm—Michael W. Glynn; Irving M. Fishman

[57] ABSTRACT

The invention relates to novel thiopyrones, especially novel benzothiopyranones of the general formula

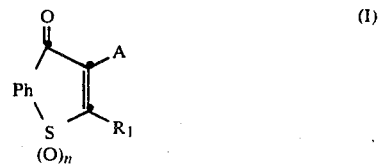

in which $R_1$ represents hydrogen or an aliphatic radical, n represents 0, 1 or 2, Ph represents substituted or unsubstituted 1,2-phenylene and A represents a group of the formula —NH—CO—R in which R represents carboxy or esterified carboxy, and to their salts, processes for the manufacture of compounds of the formula (I) and their salts, pharmaceutical preparations containing such compounds and to the use of compounds of the formula (I) and their salts as the active ingredients of medicaments and/or for the manufacture of pharmaceutical preparations. The compounds of the formula (I) and their salts have anti-allergic properties.

19 Claims, No Drawings

ANTI-ALLERGIC 3-(CARBOXYCARBONYL)AMINO BENZOTHIOPYRAN-4-ONE DERIVATIVES, COMPOSITIONS, AND METHOD OF USE THEREFOR

The invention relates to novel benzothiopyranones of the general formula

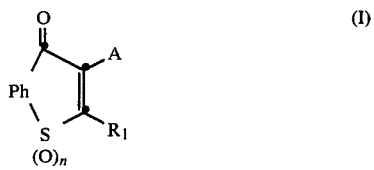

in which $R_1$ represents hydrogen or an aliphatic radical, n represents 0, 1 or 2, Ph represents substituted or unsubstituted 1,2-phenylene and A represents a group of the formula —NH—CO—R in which R represents carboxy or esterified carboxy, and to their salts, processes for the manufacture of compounds of the formula (I) and their salts, pharmaceutical preparations containing such compounds and the use of compounds of the formula (I) and their salts as the active ingredients of medicaments and/or for the manufacture of pharmaceutical preparations.

An aliphatic radical $R_1$ is especially unsubstituted and saturated, also unsaturated, and is especially a lower alkyl radical, also lower alkenyl.

1,2-phenylene may be mono- or poly-substituted, such as di-substituted, for example by an aliphatic radical, by hydroxy or hydroxy etherified by an aliphatic alcohol, by mercapto or sulpheno or sulphino substituted by an aliphatic radical, or by acyl, nitro and/or by halogen.

Aliphatic radicals as substituents of Ph are, for example, lower alkyl, lower alkenyl, lower alkynyl, 3- or 4-membered lower alkylene bridging two vicinal carbon atoms, hydroxy-lower alkyl or halo-lower alkyl.

Hydroxy etherified by an aliphatic alcohol, as a substituent of Ph, is especially lower alkoxy, hydroxy-lower alkoxy or lower alkenyloxy, while mercapto or sulpheno or sulphino substituted by an aliphatic radical is especially lower alkylthio, lower alkanesulphinyl or lower alkanesulphonyl, respectively.

Acyl is derived especially from aliphatic carboxylic acids and is especially lower alkanoyl or lower alkanoyloxy.

Esterified carboxy is, for example, carboxy esterified by an aliphatic or aromatic, especially monocyclic, alcohol, and is especially lower alkoxycarbonyl or unsubstituted or mono- or poly-substituted phenoxycarbonyl, for example phenoxycarbonyl substituted by the substituents indicated for Ph.

Hereinbefore and hereinafter, organic radicals, groups and compounds designated "lower" are to be understood as being those containing up to and including 7, especially up to and including 4, carbon atoms.

The general definitions used within the scope of the present text have, especially, the following meanings:

Lower alkyl is, for example, methyl, ethyl, n-propyl, isopropyl, n-butyl, isobutyl, sec.-butyl or tert.-butyl and also includes corresponding pentyl, hexyl or heptyl radicals.

Lower alkenyl contains, for example, at least 3 carbon atoms and has the double bond especially in a position higher than the α-position and is, for example, 2-propenyl, while lower alkynyl is, for example, propargyl.

3- or 4-membered lower alkylene has at least 3 carbon atoms, is especially straight-chained, also branched, and is, for example, tri- or tetra-methylene.

Hydroxy-lower alkyl is, for example, hydroxymethyl or 2-hydroxyethyl.

Halo-lower alkyl is, for example, chloromethyl, trifluoromethyl or 1,1,2-trifluoro-2-chloroethyl.

Lower alkoxy is, for example, methoxy, ethoxy, n-propoxy, isopropoxy, n-butoxy, isobutoxy, sec.-butoxy or tert.-butoxy, also corresponding pentyloxy, hexyloxy or heptyloxy radicals.

Hydroxy-lower alkoxy may have up to 3 hydroxy groups which are preferably bonded in a position higher than the α-position and is, for example, 2-hydroxyethoxy or 3-hydroxypropoxy.

Lower alkenyloxy has the double bond especially in a position higher than the α-position and is, for example, allyloxy, but-2-en- or but-3-en-yloxy.

Lower alkylthio is, for example, methyl-, ethyl-, n-propyl-, isopropyl-, n-butyl-, isobutyl-, sec.-butylor tert.-butyl-thio.

Lower alkane-sulphinyl or -sulphonyl is, for example, methane-, ethane-, n-propane- or isopropanesulphinyl or -sulphonyl.

Lower alkanoyl is, for example, formyl, acetyl, propionyl, butyryl, isobutyryl or pivaloyl.

Lower alkanoyloxy is, for example, acetoxy, propionyloxy, butyryloxy, isobutyryloxy or pivaloyloxy.

Halogen is, for example, halogen having an atomic number of up to and including 35, such as fluorine, chlorine or bromine, and also includes iodine.

Salts of compounds of the formula (I) according to the invention are preferably pharmaceutically acceptable salts. If R represents, for example, carboxy, corresponding salts with bases may be formed. Such salts with bases are, for example, corresponding alkali metal or alkaline earth metal salts, for example sodium, potassium or magnesium salts, pharmaceutically acceptable transition metal salts, such as zinc or copper salts, or salts with ammonia or organic amines, such as cyclic amines, such as lower alkylamines, for example mono-, di- or tri-lower alkylamines, such as hydroxy-lower alkylamines, for example mono-, di- or tri-hydroxy-lower alkylamines, such as hydroxy-lower alkyl-lower alkylamines or such as polyhydroxy-lower alkylamines. Cyclic amines are, for example, morpholine, thiomorpholine, piperidine or pyrrolidine. There come into consideration as monolower alkylamines, for example, ethyl- or tert.-butylamine, as di-lower alkylamines, for example, diethylor diisopropyl-amine, and as tri-lower alkylamines, for example, trimethyl- or triethyl-amine. Corresponding hydroxy-lower alkylamines are, for example, mono-, dior tri-ethanolamine or tris-(hydroxymethyl)-methylamine, and hydroxy-lower alkyl-lower alkylamines are, for example, N,N-dimethylamino- or N,N-diethylaminoethanol, and also glucosamine or N-methyl-D-glucamine as polyhydroxy-lower alkylamines. Also included are salts that are unsuitable for pharmaceutical uses since they can be used for the isolation or purification of free compounds according to the invention and their pharmaceutically acceptable salts.

The compounds of the formula (I) have valuable pharmacological properties. They have, especially, a pronounced anti-allergic activity. This can be demonstrated, for example, in the passive cutaneous anaphylaxis test (PCA-test) in rats in a dosage range of from approximately 0.1 to approximately 100 mg/kg in the case of oral administration, the methodology of G. E. Davies and D. P. Evans, Int. Arch. Allergy 45, 467 (1973) being used. The PCA reaction is induced analogously to the method of Z. Ovary, Progr. Allergy 5, 459 (1958).

Consequently, the active ingredients of the formula (I) can be used, for example, as anti-allergic agents in medicaments for the prophylactic and therapeutic treatment of various types of allergic disorders, especially Asthma bronchiale and allergic rhinitis.

The invention therefore also relates to the compounds of the formula (I) and their pharmaceutically acceptable salts for use in a method for the therapeutic and prophylactic treatment of the human body and to the use of the compounds for the manufacture of medicaments.

The invention relates especially to compounds of the formula (I) in which $R_1$ represents hydrogen, lower alkyl or lower alkenyl, n represents 0, 1 or 2, Ph represents 1,2-phenylene that is mono- or polysubstituted by lower alkyl, lower alkenyl, lower alkynyl, 3- or 4-membered lower alkylene bridging two vicinal carbon atoms, hydroxy-lower alkyl, halo-lower alkyl, hydroxy, lower alkoxy, hydroxy-lower alkoxy, lower alkenyloxy, lower alkylthio, lower alkanesulphinyl, lower alkanesulphonyl, lower alkanoyl, lower alkanoyloxy, nitro and/or by halogen or is unsubstituted, and A represents a group of the formula —NH—CO—R in which R represents carboxy, lower alkoxycarbonyl, or phenoxycarbonyl that is unsubstituted or mono- or poly-substituted by lower alkyl, lower alkenyl, lower alkynyl, 3- or 4-membered lower alkylene bridging two vicinal carbon atoms, hydroxy-lower alkyl, halo-lower alkyl, hydroxy, lower alkoxy, hydroxy-lower alkoxy, lower alkenyloxy, lower alkylthio, lower alkanesulphinyl, lower alkanesulphonyl, lower alkanoyl, lower alkanoyloxy, nitro and/or by halogen, and to salts, especially pharmaceutically acceptable salts.

The invention relates especially to compounds of the formula (I) in which $R_1$ represents hydrogen or lower alkyl, n represents 0, 1 or 2, Ph represents 1,2-phenylene that is mono- or poly-substituted by lower alkyl, lower alkenyl, 3- or 4-membered lower alkylene bridging two vicinal carbon atoms, hydroxylower alkyl, hydroxy, lower alkoxy, lower alkenyloxy, lower alkylthio, lower alkanesulphinyl, lower alkanesulphonyl, lower alkanoyl, lower alkanoyloxy, nitro and/or by halogen or is unsubstituted, and A represents a group of the formula—NH—CO—R in which R represents carboxy or lower alkoxycarbonyl, and to salts, especially pharmaceutically acceptable salts.

The invention relates especially to compounds of the formula (I) in which $R_1$ represents hydrogen or lower alkyl, n represents 0, Ph represents 1,2-phenylene that is mono- or poly-substituted by lower alkyl, lower alkenyl, 3- or 4-membered lower alkylene bridging two vicinal carbon atoms, lower alkoxy and/or by halogen or is unsubstituted, and A represents a group of the formula —NH—CO—R in which R represents carboxy or lower alkoxycarbonyl, and to salts, especially pharmaceutically acceptable salts.

The invention relates more especially to compounds of the formula (I) in which $R_1$ represents hydrogen, n represents 0, Ph represents 1,2-phenylene that is mono- or poly-substituted, such as di-substituted, by lower alkyl, especially having up to and including 7 carbon atoms, such as methyl, 3- or 4-membered lower alkylene bridging two vicinal carbon atoms and having from 3 up to and including 7 carbon atoms, such as trior tetramethylene, lower alkoxy, for example having up to and including 4 carbon atoms, such as methoxy, and/or by halogen, especially having an atomic number of up to and including 35, such as chlorine, or is unsubstituted, and A represents a group of the formula —NH—CO—R in which R represents carboxy or lower alkoxycarbonyl, especially having from 2 up to and including 5 carbon atoms, such as methoxycarbonyl, and to salts, especially pharmaceutically acceptable salts.

The invention relates preferably to compounds of the formula

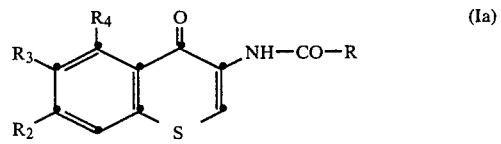

in which R represents carboxy, $R_2$ and $R_4$ represent hydrogen and $R_3$ represents hydrogen, lower alkyl having up to and including 4 carbon atoms, such as methyl, or lower alkoxy having up to and including 4 carbon atoms, such as methoxy, or in which R represents carboxy, $R_2$ and $R_3$ together represent tri- or tetra-methylene and $R_4$ represents hydrogen, and to salts, especially pharmaceutically acceptable salts.

The invention relates very especially to compounds of the formula (Ia) in which R represents carboxy, $R_2$ and $R_4$ represent hydrogen and $R_3$ represents lower alkyl having up to and including 4 carbon atoms, or in which $R_2$ and $R_3$ together represent tri- or tetra-methylene and $R_4$ represents hydrogen, or in which $R_3$ and $R_4$ together represent tri- or tetra-methylene and $R_2$ represents hydrogen, and to their salts, especially pharmaceutically acceptable salts.

The invention relates very especially to compounds of the formula (Ia) in which R represents carboxy, $R_2$ and $R_4$ represent hydrogen and $R_3$ represents lower alkyl having up to and including 4 carbon atoms, especially methyl, or in which $R_2$ and $R_3$ together represent tri- or tetra-methylene and $R_4$ represents hydrogen, and to their salts, especially pharmaceutically acceptable salts.

The invention relates specifically to the novel compounds mentioned in the Examples and to their salts, especially pharmaceutically acceptable salts, and to the processes for their manufacture described in the Examples.

The novel compounds can be manufactured in a manner known per se.

One method is carried out, for example, as follows: in a compound of the formula

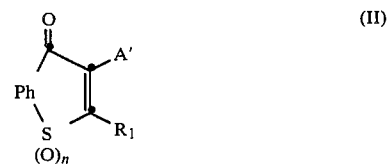

in which n, Ph and $R_1$ have the meanings indicated and A' represents a group that can be converted into A, A' is converted into A, and, if desired, a free compound obtainable according to the process is converted into a different free compound, a salt obtainable according to the process is converted into the free compound or into a different salt, a free compound obtainable according to the process is converted into a salt and/or, if desired, an isomeric mixture obtainable according to the process is separated into its components.

A group A' that can be converted into A is, for example, an amino group.

A preferred method of carrying out the process is, for example, as follows:

a compound of the formula

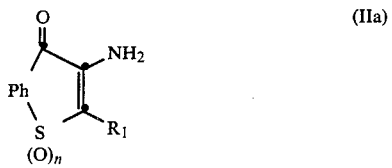

(IIa)

in which n, Ph and $R_1$ have the meanings indicated, or a salt thereof, is reacted with a compound of the formula R—$X_1$ (IIb) in which R has the meaning indicated and $X_1$ represents carboxy or functionally modified carboxy.

Salts of compounds of the formula (IIa) are, for example, acid addition salts, such as corresponding hydrohalides or lower alkanoates. Functionally modified carboxy should be understood as being, for example, reactive esterified, anhydridised or also amidated carboxy. Esterified carboxy $X_1$ may have, for example, the meanings given at the beginning for R, while there comes into consideration as anhydridised carboxy, for example, carboxy anhydridised by a mineral acid, such as a hydrohalic acid, or by a carboxylic acid, such as a lower alkanecarboxylic acid or carbonic acid halide lower alkyl semi-ester.

Amidated carboxy has, for example, a free or mono- or di-substituted amino group. A mono-substituted amino group is mono-substituted, for example, by an aliphatic radical, by an araliphatic radical or by an aromatic radical. A di-substituted amino group has aliphatic and/or araliphatic radicals as substituents.

An aliphatic radical as substituent of carbamoyl is especially a saturated aliphatic radical, especially lower alkyl. A corresponding araliphatic radical has as the aryl moiety especially monocyclic aryl, such as optionally substituted phenyl, and the aliphatic moiety is saturated and is especially lower alkyl. Corresponding substituents are especially phenyl-lower alkyl that is unsubstituted or substituted in the phenyl moiety. An aromatic radical as substituent of carbamoyl is especially a monocyclic aromatic radical and is especially phenyl that is unsubstituted or substituted as indicated above for phenyl. Carbamoyl containing substituted phenyl may be mono- or polysubstituted in the phenyl moiety by lower alkyl, lower alkoxy, hydroxy, lower alkanoyloxy, nitro, halogen and/or by trifluoromethyl. There comes into consideration as aliphatic radical in N,N-disubstituted carbamoyl also alkylene or alkylene interrupted by monoaza, N-alkylated monoaza, mono-oxa or monothia, especially corresponding lower alkylene. There may be mentioned as examples of carboxy amidated in that manner, for example, carbamoyl, N-mono- or N,N-di-lower alkylcarbamoyl, N-mono- or N,N-di-lower alkylphenylcarbamoyl, N-monophenylcarbamoyl, N-(5-tetra- zolyl)-carbamoyl, lower alkylenecarbamoyl or lower alkylenecarbamoyl interrupted by monoaza, N'-lower alkylaza, mono-oxa or monothia.

There are used for the above reaction especially those compounds of the formula (IIb) in which $X_1$ represents carboxy or halocarbonyl, such as chlorocarbonyl.

The amidation can be carried out in the manner known for analogous reactions. For example, a condensation agent may be necessary. The reaction according to the process (N-acylation) is, if necessary, carried out in the presence of a condensation agent, especially a basic condensation agent. Suitable bases are, for example, alkali metal hydroxides, hydrides, amides, alkoxides, carbonates, triphenyl methylides, di-lower alkylamides, aminoalkylamides or lower alkylsilylamides, naphthaleneamines, lower alkylamines, basic heterocycles, ammonium hydroxides and carbocyclic amines. There may be mentioned by way of example sodium hydroxide, hydride or amide, potassium tert.-butoxide or carbonate, lithium triphenyl methylide or diisopropylamide, potassium 3-(aminopropyl)-amide or bis-(trimethylsilyl)-amide, dimethylaminonaphthalene, di- or tri-ethylamine, pyridine, benzyltrimethylammonium hydroxide, 1,5-diazabicyclo[4.3.0]non-5-ene (DBN) and 1,8-diazabicyclo[5.4.0]undec-7-ene (DBU). Included among the condensation agents are the dehydration agents customarily employed in the formation of amide compounds; these agents are used especially when $X_1$ in the formula (IIb) represents carboxy. For example, it is possible for reactive carboxy derivatives of the formula (IIb), especially corresponding activated esters or amides, to be formed in situ. Suitable dehydration agents are, for example, carbodiimides, for example N,N'-di-lower alkyl or N,N'-dicycloalkyl carbodiimide, such as N,N'diethyl, N,N'-diisopropyl or N,N'-dicyclohexyl carbodiimide, advantageously with the addition of N-hydroxysuccinimide, or optionally substituted, for example halo-, lower alkyl- or lower alkoxy-substituted, 1-hydroxybenzotriazole or N-hydroxy-5-norbornene-2,3-dicarboxamide, N,N'-diimidazolecarbonyl, a suitable phosphoryl or phosphine compound, for example diethylphosphoryl cyanide, diphenylphosphorylazide or triphenylphosphine disulphide, a 1-lower alkyl-2-halopyridinium halide, for example 1-methyl-2-chloropyridinium iodide, a suitable 1,2-dihydroquinoline, for example N-ethoxycarbonyl-2-ethoxy1,2-dihydroquinoline, or 1,1'-(carbonyldioxy)dibenzotriazole. In the case of the reaction with a compound of the formula (IIb) in which R represents an esterified carboxy group and $X_1$ represents halocarbonyl, there is used, for example, a basic condensation agent, such as an organic nitrogen base, for example triethylamine or pyridine, or such as an alkali metal hydroxide or carbonate, for example sodium or potassium hydroxide. In the case of the reaction with a corresponding compound of the formula (IIb) in which $X_1$ represents carboxy it is also possible, for example, to use a carbodiimide or isonitrile, such as dicyclohexyl carbodiimide or tert.-butylisonitrile, as dehydration agent, also a mineral acid, such as hydrochloric acid, or an acid anhydride, such as phosphorus pentoxide. The amidation is carried out, for example, in the presence or absence of a solvent or diluent, such as a halogenated hydrocarbon, for example chloroform. It is preferable to use equimolar amounts of corresponding compounds of the formulae (IIa) and (IIb).

The starting materials of the formulae (IIa) and (IIb) are known or can be manufactured analogously to customary processes.

For example, compounds of the formula (IIa) are obtained by reducing compounds of the formula

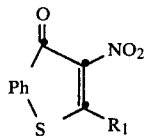 (IIf)

to compounds of the formula (IIa) in which n represents zero. The reduction is carried out, for example, with hydrogen under the catalytic action of palladium/carbon.

For the manufacture of compounds of the formula (IIa) in which n represents 1 or 2, for example compounds of the formula (IIa) in which n is zero are used as starting materials and the amino group is protected, for example by acetylation using acetic anhydride. If approximately one equivalent of an oxidising agent, for example m-chloroperbenzoic acid, is used, compounds of the formula (IIa) can be obtained in which n represents 1, while oxidation with at least 2 mol of oxidising agent results in corresponding compounds of the formula (IIa) in which n represents 2.

In the next reaction step, the amino-protecting group is removed again. For example, an acetyl group is removed hydrolytically by treatment with ethanolic hydrochloric acid.

A preferred method of manufacturing compounds of the formula (IIa) in which $R_1$ represents hydrogen is to react compounds of the formula

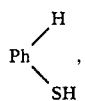 (IId)

or salts thereof, with a halopropionic acid, such as bromopropionic acid, and to cyclise the resulting compounds of the formula

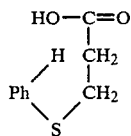 (IIe)

in the presence of a strong acid, such as sulphuric acid, to form compounds of the formula

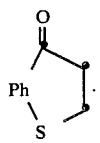 (IIf)

These are then treated, for example, with isopentyl nitrite in potassium hydroxide solution and the resulting compounds of the formula

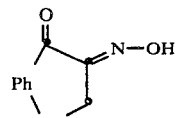 (IIg)

are reacted with hydrochloric or hydrobromic acid. Corresponding compounds of the formula

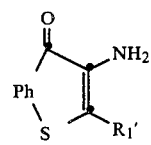 (IIh)

are formed in which $R_1'$ represents hydrogen or chlorine or bromine. By reduction with, for example, hydrogen in the presence of palladium/carbon the chlorine or bromine atom in corresponding compounds of the formula (IIh) can be replaced by hydrogen.

In the manner described above, from the resulting compounds of the formula (IIa) in which n represents zero and $R_1$ represents hydrogen it is possible to obtain corresponding S-oxidised compounds.

A further group A' that can be converted into A is, for example, a group of the formula —NH—CO—X2 in which $X_2$ represents a radical that can be converted into R by solvolysis, such as hydrolysis or alcoholysis. Suitable as such a radical $X_2$ is, for example, functionally modified carboxy other than R; there may be mentioned, especially, cyano, anhydridised carboxy, such as halocarbonyl, lower alkanoyloxycarbonyl or lower alkoxycarbonyloxycarbonyl, amidated carboxy such as mentioned above, optionally substituted amidino, such as lower alkylamidino, optionally esterified thiocarboxy, such as lower alkylthiocarbonyl, optionally esterified dithiocarboxy, optionally substituted thiocarbamoyl, such as mono- or di-lower alkylthiocarbamoyl, optionally esterified or anhydridised carboximidoyl, such as lower alkoxy- or halo-iminocarbonyl, or radicals derived from orthoformic acid esters, such as tri-lower alkoxy- or trihalo-methyl.

Solvolysis agents are, for example, water or alcohols that correspond to the desired esterified carboxy group.

The treatment with a corresponding solvolysis agent is optionally carried out in the presence of an acid or base, optionally while cooling or heating and, if necessary, in an inert solvent or diluent. Suitable acids are, for example, inorganic or organic protonic acids, such as mineral acids, for example sulphuric acid or a hydrohalic acid, such as sulphonic acids, for example a lower alkanesulphonic acid or optionally substituted benzenesulphonic acid, or such as carboxylic acids, such as lower alkanecarboxylic acids. As bases it is possible to use, for example, hydroxides, such as alkali metal hydroxides.

For example, the cyano group, amidated carboxy such as mentioned above, optionally esterified thiocarboxy, optionally esterified dithiocarboxy, optionally substituted thiocarbamoyl, optionally esterified or anhydridised carboximidoyl, or radicals $X_2$ derived from orthoformic acid, can be hydrolysed to carboxy R optionally in the presence of a protonic acid, while, for example, cyano, optionally S-esterified thiocarboxy or anhydridised carboxy $X_2$ can be alcoholised to esterified carboxy R using a suitable alcohol, optionally in the presence of a protonic acid.

The removal of corresponding amino-protecting groups is carried out especially by acidolysis or reduction. Suitable acids are, for example, optionally substituted lower alkanecarboxylic acids, such as trifluoroacetic acid, hydrohalic acids, such as hydrofluoric acid, or mixtures of hydrohalic acids with lower alkanecarboxylic acids, such as mixtures of hydrobromic acid and acetic acid. The removal by reduction is carried out, for example, by reduction with hydrogen produced in statu nascendi or by catalytically activated hydrogen. For example, hydrogen is produced in systems, such as zinc-/acetic acid or sodium/ammonia, while, for example, a noble metal or a derivative thereof, such as platinum, rhodium, palladium or platinum oxide, also Raney nickel, is used as catalyst for the activation of hydrogen.

The removal of the amino-protecting group is carried out in the presence or absence of an inert solvent or diluent, if necessary while cooling and/or heating.

A' can also be converted into A by oxidation, A' representing a group of the formula —NH—CO—$X_2$ and $X_2$ representing optionally esterified or etherified hydroxymethyl or optionally hydrated formyl.

Esterified hydroxymethyl is, for example, hydroxymethyl esterified by an aliphatic carboxylic acid. Suitable aliphatic carboxylic acids are especially lower alkanecarboxylic acids.

Etherified hydroxymethyl is, for example, hydroxymethyl etherified by an aliphatic alcohol that is especially saturated, especially by a lower alkanol.

Optionally hydrated formyl can advantageously be formed in situ in the course of the oxidation reaction, for example from an optionally esterified hydroxymethyl group, or it can be freed from one of its functional derivatives, for example one of its acetals or imines. Corresponding esterified hydroxymethyl groups are, for example, hydroxymethyl groups esterified at the hydroxy group by a mineral acid, such as a hydrohalic acid, for example by hydrochloric or hydrobromic acid, or by a carboxylic acid, such as a lower alkanecarboxylic acid or optionally substituted benzoic acid. Acetalised formyl groups are, for example, formyl groups acetalised by lower alkanols or a lower alkanediol, such as dimethoxy, diethoxy, ethylenedioxy or trimethylenedioxy groups. Iminomethyl groups are, for example, optionally substituted N-benzylimino- or N-(2-benzothiazolyl)-imino-methyl. Hydroxymethyl groups $X_2$ or optionally hydrated formyl groups $X_2$ can be oxidised to carboxy R and etherified hydroxymethyl groups can be oxidised to esterified carboxy R.

The oxidation can be carried out in customary manner by reaction with a suitable oxidising agent. Suitable oxidising agents are especially oxidising heavy metal compounds, such as silver compounds, for example silver nitrate or silver picolinate, oxy acids of heavy metals, for example of manganese(IV), manganese(VII), chromium(VI) and iron(III), or of halogens or anhydrides or salts thereof, such as chromic acid, chromium dioxide, potassium dichromate, potassium permanganate, manganese dioxide, potassium ferrate, sodium chlorite in the presence of sulphamic acid, sodium hypochlorite in the presence of nickel chloride, or sodium iodate, sodium periodate or lead tetraacetate. The reaction with these oxidising agents is carried out in customary manner, for example in an inert solvent, such as acetone, acetic acid, pyridine or water, or an inert solvent mixture, preferably an aqueous inert solvent mixture, at normal temperature or, if necessary, while cooling or heating, for example at from approximately 0° to approximately 100° C. The oxidation of optionally etherified hydroxymethyl groups $X_2$ to optionally esterified carboxy groups R is carried out, for example, advantageously with potassium permanganate in aqueous pyridine or acetone at room temperature. Acetalised formyl groups $X_2$ and iminomethyl groups $X_2$ are preferably oxidised acidically, for example using potassium dichromate in sulphuric acid, while potassium ferrate in an alkaline medium, for example at pH=10-13, for example 11.5, or organic silver salts, such as silver picolinate, are preferably used for the oxidation of the formyl group.

The starting materials of the formula (II) can, if they are novel, be manufactured according to methods known per se.

For example, compounds of the formula

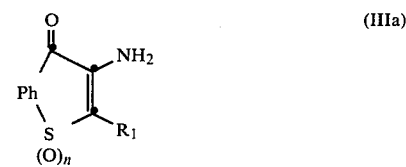

(IIIa)

are reacted with one equivalent of a compound of the formula $X_1$-$X_2$ (IIIb) in which $X_1$ and $X_2$ have the meanings indicated above.

There are used for the above reaction especially those compounds of the formula (IIIb) in which $X_1$ represents carboxy or halocarbonyl.

The novel compounds can also be manufactured as follows: a compound of the formula

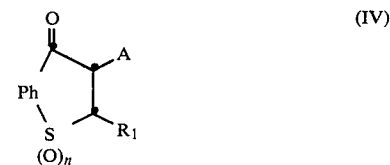

(IV)

in which n, Ph, A and $R_1$ have the meanings indicated, or a salt thereof, is dehydrogenated to form the corresponding compound of the formula (I) and, if desired, a free compound obtainable according to the process is converted into a different free compound, a salt obtainable according to the process is converted into the free compound or into a different salt, a free compound obtainable according to the process is converted into a salt and/or, if desired, an isomeric mixture obtainable according to the process is separated into its components.

The dehydrogenation of compounds of the formula (IV) or salts thereof is carried out in a manner known per se, advantageously at elevated temperature, for example in a temperature range of from approximately 50° to approximately 300° C., with the aid of a dehydrogenation agent. Such agents are, for example, dehydrogenation catalysts, for example elements of the sub-groups, preferably those of sub-group VIII, such as palladium or platinum, or corresponding salts, such as ruthenium triphenyl phosphide chloride, it being possible for the catalysts to be supported on suitable carriers, such as activated carbon, aluminium oxide or silica. Further suitable dehydrogenation agents are, for example, quinones, such as p-benzoquinones, for example tetrachloro-p-benzoquinone or 2,3-dichloro-5,6-dicyano-p-benzoquinone, or such as anthraquinones, for example phenanthrene-9,10-quinone, N-halosuccinimides, such as N-chlorosuccinimide, or selenium derivatives, such as selenium dioxide or diphenylselenium bis-trifluoroacetate, also selenium or sulphur. It is also possible to use as dehydrogenation agents especially tritylium salts, such as tritylium perchlorate or tetrafluoroborate.

The reaction is optionally carried out in an inert high-boiling solvent, such as an ether, for example diphenyl ether, if necessary at elevated temperature, under pressure, in a closed vessel and/or under an inert gas, for example nitrogen.

The starting compounds of the formula (IV) or their salts can be manufactured according to methods known per se. For example, compounds of the formula

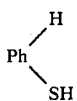 (IVa)

are used as starting materials and are reacted with compounds of the formula

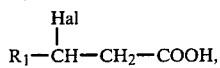 (IVb)

or a functional derivative thereof, in which Hal represents halogen, such as chlorine, in the presence of a strong acid, such as sulphuric acid or polyphosphoric acid, to form compounds of the formula

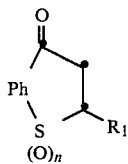 (IVc)

in which n is zero. These can, if desired, be S-oxidised by treatment with a suitable oxidising agent, such as m-chloroperbenzoic acid; an SO compound is obtained if one equivalent of oxidising agent is used and a corresponding $SO_2$ compound is obtained in the case of reaction with at least 2 mol of oxidising agent.

The reaction of compounds of the formula (IVc) in which n is 0, 1 or 2 with hydroxylamine results in corresponding oximes which can then be reacted by treatment with p-toluenesulphonyl chloride to form corresponding sulphonyl esters of the formula

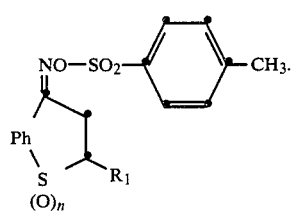 (IVd)

The treatment of these compounds of the formula (IVd) with sodium methoxide and the subsequent acid hydrolysis and neutralisation results in amines of the formula

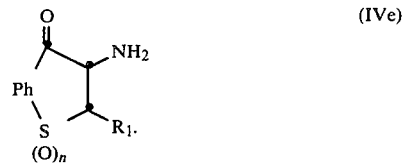 (IVe)

In the further course of the reaction sequence, the amino group can be converted into the grouping A by reaction with a compound of the formula $R-X_1$ (IIb) in which $X_1$ has the meaning given at the beginning, especially with an acid halide. There result from this reaction the corresponding starting compounds of the formula (IV).

Another method of manufacturing compounds of the formula (I) in which $R_1$ represents hydrogen, or salts thereof, is as follows:

in a compound of the formula

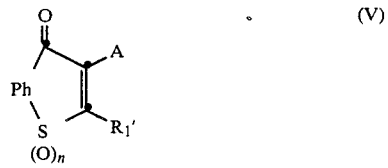 (V)

in which n, Ph and A have the meanings indicated, and $R_1'$ represents a radical that can be converted into $R_1$, the radical $R_1'$ is converted into $R_1$ and, if desired, a free compound obtainable according to the process is converted into a different free compound, a salt obtainable according to the process is converted into the free compound or into a different salt, a free compound obtainable according to the process is converted into a salt and/or, if desired, an isomeric mixture obtainable according to the process is separated into its components.

Radicals $R_1'$ that can be converted into $R_1$ are, for example, carboxy or halogen, especially chlorine or bromine, also iodine.

The decarboxylation of compounds of the formula (V) in which $R_1'$ represents carboxy, or salts thereof, is normally carried out while heating, for example in a temperature range of from approximately 100° to approximately 300° C., optionally in the presence of a transition metal or an alloy thereof, for example copper or copper-bronze, or in the presence of a base, such as a basic nitrogen heterocycle, for example pyridine or quinoline, or an alkylamine, such as a tri-lower alkylamine.

The reductive conversion of compounds of the formula (V) in which $R_1'$ represents halogen, or salts thereof, is carried out, for example, by hydrogenation in the presence of a hydrogenation catalyst, such as an element of sub-group VIII of the Periodic Table or a derivative thereof, for example an oxide, it being optionally possible for the catalyst to be supported on a suitable carrier, such as activated carbon or barium carbonate.

There may be mentioned as examples of such catalysts the customary hydrogenation catalysts, especially Raney nickel or palladium/carbon. If necessary, the hydrogenation is carried out in the presence of an acid or, especially, of a base. Suitable acids are protonic acids, such as mineral acids, for example hydrohalic acids, also carboxylic acids, such as lower alkanecarboxylic acids. Suitable bases are, for example, alkali metal hydroxides, carbonates or acetates, amines, such as lower alkylamines, or basic heterocycles, such as pyridine or quinoline.

Furthermore, halogen R₁' can be converted into hydrogen R₁ by treatment with red phosphorus and/or hydriodic acid, for example by heating at from approximately 100° to approximately 250° C.

The starting materials of the formula (V) are manufactured according to the processes described in the literature for analogous reactions.

For the manufacture of compounds of the formula (V) in which R₁' represents carboxy there are used as starting materials, for example, compounds of the formula

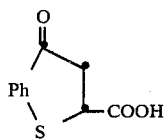
(Va)

and these are converted, if desired, using a suitable oxidising agent, such as m-chloroperbenzoic acid, into the S-oxides and these or the compounds of the formula (Va) are reacted with hydroxylamine to form the corresponding oximes which are subsequently esterified by p-toluenesulphonyl chloride to form compounds of the formula

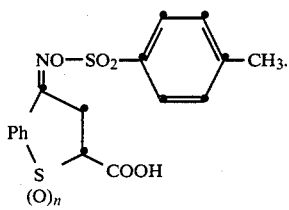
(Vb)

After treatment of these compounds with one of the above-mentioned dehydrogenation agents, such as tritylium perchlorate, and then with potassium methoxide, and subsequent acid hydrolysis and neutralisation, amines of the formula

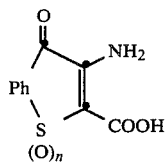
(Vc)

are obtained. In the subsequent reaction step, the compounds of the formula (Vc) can be converted by reaction with a compound of the formula R—X₁ (IIb) in which X₁ has the meaning given at the beginning, especially with an acid halide, into the corresponding starting materials of the formula (V) in which R₁' represents carboxy.

Starting compounds of the formula (V) in which R₁' represents halogen, especially chlorine or bromine, also iodine, can be manufactured as follows. There are used as starting materials, for example, compounds of the formula

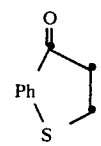
(Ve)

and these are reacted with isopentyl nitrite in potassium hydroxide solution, corresponding compounds of the formula

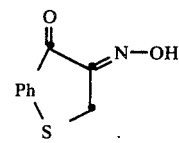
(Vf)

being formed. These are for their part treated with a hydrohalic acid, especially hydrochloric or hydrobromic acid. From these there are obtained corresponding compounds of the formula

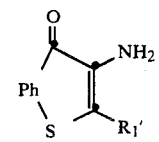
(Vg)

in which R₁' represents halogen.

If corresponding compounds of the formula (V) are desired in which n represents 1 or 2, these compounds of the formula (Vg) can, after protection of the amino group, be correspondingly S-oxidised using a suitable oxidising agent, such as m-chloroperbenzoic acid. After removing the amino-protecting group, in the subsequent reaction step the amino group in compounds of the formula (Vg) or their S-oxides can be converted into the desired group A by reaction with an acid of the formula R—COOH (Vf) or a reactive derivative, for example an acid halide, thereof.

The compounds of the formula I according to the invention can also be manufactured as follows: a compound of the formula

(VI)

in which Ph has the meaning indicated and X₄ represents a group of the formula —S(O)$_n$—C(R₁)=C(A)—X₅ in which X₅ represents optionally functionally modified carboxy, or a salt thereof, is cyclised and, if desired, a free compound obtainable according to the process is converted into a different free compound, a salt obtainable according to the process is converted into the free compound or into a different salt, a free compound obtainable according to the process is converted into a salt and/or, if desired, an isomeric mixture obtainable according to the process is separated into its components.

Functionally modified carboxy is especially esterified or anhydridised carboxy. Esterified carboxy is preferably carboxy esterified by a lower alkanol, such as lower alkoxycarbonyl, while anhydridised carboxy is, for example, carboxy anhydridised by a lower alkanecarboxylic acid or an optionally substituted benzoic acid or, especially, by a hydrohalic acid or a carbonic acid halide lower alkyl semi-ester, such as lower alkanoyloxycarbonyl or benzoyloxycarbonyl, halocarbonyl or lower alkoxycarbonyloxycarbonyl.

The cyclisation is effected intramolecularly and can be carried out, especially, in the manner known from the literature for analogous reactions, if necessary in the presence of a condensation agent and/or at elevated temperature, for example at the boiling temperature of the solvent.

Suitable condensation agents are, for example, strong inorganic or organic protonic acids, such as mineral acids, for example hydrohalic acids, sulphuric acid or polyphosphoric acid, such as sulphonic acids, for example alkanesulphonic acids or optionally substituted benzenesulphonic acids, for example p-toluenesulphonic acid, or such as organic carboxylic acids, for example lower alkanecarboxylic acids, for example acetic acid. It is also possible to use Lewis acids for the cyclisation, for example compounds of elements of main groups III and V and of sub-groups II and VIII of the Periodic Table. There come into consideration especially halides of boron, aluminium, tin, antimony and iron, such as boron trifluoride, aluminium chloride, tin(IV) chloride, zinc chloride and iron(III) chloride.

The starting materials are known or, if they are novel, can be manufactured according to methods known per se.

For example, starting materials of the formula VI in which $X_4$ represents a group of the formula $-S(O)_n-C(R_1)=C(A)-X_5$ and n represents zero can be manufactured by condensing compounds of the formula

(VIa)

with compounds of the formula

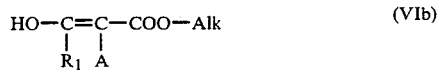

(VIb)

in which Alk represents lower alkyl, with the aid of a condensation agent, such as polyphosphoric acid, to form the corresponding compounds of the formula (VI).

The compounds of the formula (VIb) can be obtained by reacting compounds of the formula $HO-C(R_1)=C(NH_2)-COO-Alk$ (VIc) or tautomers thereof with compounds of the formula $R-COOH$ (VId) or functional derivatives thereof, especially with corresponding acid halides.

The compounds of the formula (VIc) are for their part known or can be manufactured according to processes known per se. For example, they can be obtained by treating compounds of the formula $R_1-CO-CH_2-CO-Alk$ (VId) in acetic acid with sodium nitrite and, in resulting compounds of the formula $R_1-CO-C(=NOH)-CO-Alk$ (VIe), reducing the hydroxyimino group with hydrogen in the presence of hydrochloric acid.

Another method of manufacturing the compounds of the formula (I) according to the invention is as follows:

in a compound of the formula

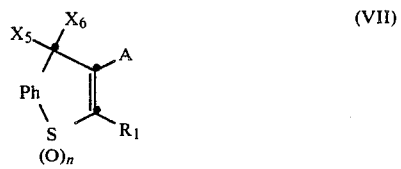

(VII)

in which A, $R_1$, n and Ph have the meanings indicated and $X_5$ and $X_6$ represent radicals that can together be converted into the oxo group, or in a salt thereof, $X_5$ and $X_6$ are converted into the oxo group and, if desired, a free compound obtainable according to the process is converted into a different free compound, a salt obtainable according to the process is converted into the free compound or into a different salt, a free compound obtainable according to the process is converted into a salt and, if desired, an isomeric mixture obtainable according to the process is separated into its components.

Radicals $X_5$ and $X_6$ that can be converted into the oxo group may together form functionally modified oxo, such as thioxo, optionally substituted imino, lower alkylenedioxy, lower alkylenedithioxy or, independently of one another, lower alkoxy or lower alkylthio. $X_5$ and $X_6$ can together be converted by hydrolysis into the oxo group. If necessary the operation is carried out in the presence of a catalytic agent, such as a protonic acid, in an inert solvent and while heating, for example at from approximately 50° to approximately 150° C. Suitable protonic acids are, for example, mineral acids, such as hydrohalic acids or sulphuric acid, aliphatic carboxylic acids, such as lower alkanecarboxylic acids, or sulphonic acids, such as optionally substituted benzenesulphonic acids.

A substituted imino group can be substituted, for example, by an aliphatic or aromatic radical, such as lower alkyl or phenyl, or by an acyl radical that is derived from a carboxylic acid or a semi-ester of carbonic acid, such as lower alkanoyl, benzoyl or lower alkoxycarbonyl.

The starting material of the formula (VII) in which $X_5$ and $X_6$ together form thioxo is obtained, for example, by reacting compounds of the formula

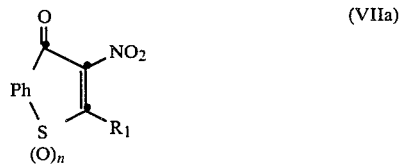

(VIIa)

with phosphorus pentasulphide in the presence of sodium bicarbonate or with silicon disulphide while heating. Corresponding thioketals can be obtained, for example, by reacting compounds of the formula (VIIa) with mercapto compounds, the operation being carried out in the presence of hydrochloric acid, and corresponding O-acetals can be obtained analogously by reaction with alcohols and p-toluenesulphonic acid. Corresponding imines are obtained by reacting compounds of the formula (VIIa) with ammonia or primary amines in the presence of hydrochloric acid, sodium hydroxide or zinc chloride. The resulting compounds are then reduced to compounds of the formula

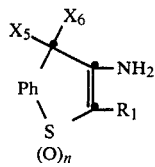
(VIIb)

or salts thereof and converted into the corresponding compounds of the formula (VII) by reaction with compounds of the formula R-$X_1$ (IIb) in which $X_1$ has the meanings indicated at the beginning, for example with carboxylic acid halides.

The reactions described hereinbefore and hereinafter are carried out according to processes known per se, for example in the absence, or usually in the presence, of a suitable solvent or diluent or a mixture thereof, the operation being carried out, depending on the method used, while cooling, at room temperature or while heating, for example in a temperature range of from approximately $-20°$ C. up to the boiling temperature of the reaction medium, and, if necessary, in a closed vessel, under pressure, in an inert gas atmosphere and/or under anhydrous conditions.

The starting materials mentioned hereinbefore and hereinafter, which were developed for the manufacture of the compounds of the formula I and salts thereof, are in some cases known or can be manufactured according to methods known per se, for example analogously to the process variants described hereinbefore and hereinafter.

A compound of the formula (I) that is obtainable according to the invention or by other methods can be converted into a different compound of the formula (I) in a manner known per se.

For example, compounds of the formula (I) in which 1,2-phenylene Ph contains hydrogen can be halogenated, such as chlorinated or brominated, by reacting corresponding compounds in a temperature range of from approximately 0° to approximately 150° C. with a suitable halogenating agent, such as chlorine or bromine, in a non-polar solvent, such as methylene chloride, optionally in the presence of a Lewis acid.

In addition, the benzo moiety of the ring system can be alkylated, for example, with a lower alkanol or a lower alkyl halide or a phosphoric acid lower alkyl ester in the presence of Lewis acids. In a compound of the formula (I) in which 1,2-phenylene Ph contains, for example, bromine, the bromine can, for example, be replaced by lower alkyl by reaction with a lower alkyl bromide in the presence of an alkali metal, especially lithium.

If 1,2-phenylene Ph contains hydroxy as substituent, this hydroxy can be etherified in a manner known per se. The reaction with an alcohol component, for example with a lower alkanol, such as ethanol, in the presence of acids, for example mineral acids, such as sulphuric acid, or dehydrating agents, such as dicyclohexyl carbodiimide, results in lower alkoxy. Conversely, ethers can be cleaved to form phenols by cleavage by means of acids, such as mineral acids, for example hydrohalic acids, such as hydrobromic acid, or Lewis acids, for example halides of elements of main group III, such as boron tribromide, or by means of a pyridinium hydrohalide, for example pyridinium hydrochloride, or thiophenol.

In addition, hydroxy can be converted into lower alkanoyloxy, for example by reaction with a desired lower alkanecarboxylic acid, such as acetic acid, or a reactive derivative thereof, for example in the presence of an acid, such as a protonic acid, for example hydrochloric, hydrobromic, sulphuric or phosphoric acid or a benzenesulphonic acid, in the presence of a Lewis acid, for example boron trifluoride etherate, or in the presence of a water-binding agent, such as dicyclohexyl carbodiimide. Conversely, esterified hydroxy can be solvolysed, for example by base catalysis, to form hydroxy.

Free and esterified carboxy groups R can be converted into one another; for example a free carboxy group can be converted in customary manner into an esterified carboxy group R, preferably by reaction with a corresponding alcohol or a reactive derivative, such as a carboxylic, phosphorous, sulphurous or carbonic acid ester, for example a lower alkanecarboxylic acid ester, a tri-lower alkyl phosphite, a di-lower alkyl sulphite or a pyrocarbonate, or a mineral acid ester or a sulphonic acid ester, for example the hydrochloric, hydrobromic, sulphuric, benzenesulphonic, toluenesulphonic or methanesulphonic acid ester, of the corresponding alcohol or with an olefin derived therefrom.

The reaction with the corresponding alcohol is advantageously carried out in the presence of an acidic catalyst, such as a protonic acid, for example hydrochloric, hydrobromic, sulphuric, phosphoric, boric, benzenesulphonic and/or toluenesulphonic acid, or a Lewis acid, for example boron trifluoride etherate, in an inert solvent, especially an excess of the alcohol used, and, if necessary, in the presence of a water-binding agent and/or while removing the water of reaction by distillation, for example azeotropic distillation, and/or at elevated temperature.

The reaction with a reactive derivative of the corresponding alcohol can be carried out in customary manner; when starting from a carboxylic, phosphorous, sulphurous or carbonic acid ester, the reaction is carried out, for example, in the presence of an acidic catalyst, such as one of those mentioned above, in an inert solvent, such as an aromatic hydrocarbon, for example in benzene or toluene, or an excess of the alcohol derivative used or of the corresponding alcohol, if necessary while distilling off the water of reaction, for example azeotropically. When starting from a mineral or sulphonic acid ester, the acid to be esterified is advantageously reacted in the form of a salt, for example the sodium, potassium or calcium salt, for example in the presence of a basic condensation agent, such as an inorganic base, for example sodium, potassium or calcium hydroxide or carbonate, or a tertiary organic nitrogen base, for example triethylamine or pyridine, if necessary in an inert solvent, such as one of the above tertiary nitrogen bases, or a polar solvent, for example in dimethylformamide, and/or at elevated temperature.

The reaction with an olefin can be carried out, for example, in the presence of an acid catalyst, for example a Lewis acid, for example boron trifluoride, a sulphonic acid, for example toluenesulphonic acid, or especially a basic catalyst, for example sodium or potassium hydroxide, advantageously in an inert solvent, such as an ether, for example in diethyl ether or tetrahydrofuran.

The above-described conversions of free carboxy groups R into esterified carboxy groups R can, however, alternatively be carried out as follows: a compound of the formula I in which R represents carboxy is first of all converted in customary manner into a reactive derivative, for example, by means of a halide of phosphorus or sulphur, for example by means of phosphorus trichloride or tribromide, phosphorus pentachloride or thionyl chloride, into an acid halide, or, by reaction with a corresponding alcohol or amine, into a reactive ester, that is to say an ester with electron attracting structures, such as an ester with phenol, thiophenol, p-nitrophenol or cyanomethyl alcohol, or into a reactive amide, for example the amide derived from imidazole or 3,5-dimethylpyrazole, and the resulting reactive derivative is then reacted in customary manner, for example as described below for the transesterification or conversion into one another of esterified carboxy groups R, with a corresponding alcohol to form the desired group R.

An esterified carboxy group R can also be reacted to form a different esterified carboxy group R in customary manner, for example by reaction with a corresponding metal alcoholate, for example the sodium or potassium alcoholate of the corresponding alcohol, or with the alcohol itself in the presence of a catalyst, for example a strong base, for example sodium or potassium hydroxide, or a strong acid, such as a mineral acid, for example hydrochloric acid, sulphuric acid or phosphoric acid, or an organic sulphonic acid, for example p-toluenesulphonic acid, or a Lewis acid, for example boron trifluoride etherate.

An amidated carboxy group R can be converted into a free carboxy group R in customary manner, for example by hydrolysis in the presence of a catalyst, for example a strong base, such as an alkali metal or alkaline earth metal hydroxide or carbonate, for example sodium or potassium hydroxide or carbonate, or a strong acid, such as a mineral acid, for example hydrochloric acid, sulphuric acid or phosphoric acid.

If n in the formula (I) represents zero, the sulphur atom can be oxidised in customary manner to form corresponding sulphinyl or sulphonyl. There come into consideration as suitable oxidising agents for the oxidation to the sulphoxide stage, for example, inorganic peracids, such as peracids of mineral acids, for example periodic acid or persulphuric acid, organic peracids, such as corresponding percarboxylic or persulphonic acids, for example performic, peracetic, trifluoroperacetic or m-chloroperbenzoic acid or p-toluenepersulphonic acid, or mixtures of hydrogen peroxide and acids, for example a mixture of hydrogen peroxide and acetic acid.

The oxidation is often carried out in the presence of suitable catalysts; there may be mentioned as catalysts suitable acids, such as optionally substituted carboxylic acids, for example acetic acid or trifluoroacetic acid, or transition metal oxides, such as oxides of elements of sub-group VII, for example vanadium, molybdenum or tungsten oxide. The oxidation is carried out under mild conditions, for example at temperatures of from approximately −50° to approximately +100° C.

The oxidation to the sulphone stage can be carried out correspondingly with dinitrogen tetroxide as the catalyst in the presence of oxygen at low temperatures, as can the direct oxidation of the thio to the sulphonyl. In this case, however, the oxidising agent is normally used in excess. The oxidation of mercapto or sulpheno that is substituted by an aliphatic radical and is a substituent of Ph can be carried out in a corresponding manner.

In compounds of the formula I in which n represents 1 or 2, the sulphinyl or sulphonyl group can be reduced to thio. The reduction to corresponding sulpheno or mercapto of sulphonyl or sulphinyl that is substituted by an aliphatic radical and is a substituent of Ph can be carried out in a corresponding manner. Suitable reducing agents are, for example, catalytically activated hydrogen, there being used noble metals or oxides, such as palladium, platinum or rhodium or their oxides, optionally supported on a suitable carrier, such as activated carbon or barium sulphate. Also suitable are reducing metal cations, such as tin(II), lead(II), copper(I), manganese(II), titanium(II), vanadium(II), molybdenum-(III) or tungsten(III) compounds, hydrogen halides, such as hydrogen chloride, bromide or iodide, hydrides, such as complex metal hydrides, for example lithium aluminium hydride, sodium borohydride, tributyltin hydride, phosphorus compounds, such as phosphorus halides, for example phosphorus trichloride, phosphorus tribromide, phosphorus pentachloride or phosphorus oxychloride, phosphines, such as triphenylphosphine, or phosphorus pentasulphide pyridine, or sulphur compounds, such as mercaptans, thio acids, such as thiophosphoric acids or dithiocarboxylic acids, dithionite or sulphur-oxygen complexes, such as an iodine/pyridine/sulphur dioxide complex.

If the compounds of the formula (I) contain unsaturated radicals, such as lower alkenyl groupings, these can be converted in a manner known per se into saturated radicals. For example, the hydrogenation of multiple bonds is carried out by catalytic hydrogenation in the presence of hydrogenation catalysts, there being suitable for this purpose, for example, noble metals or derivatives, for example oxides, thereof, such as nickel, Raney nickel, palladium, and platinum oxide, which may optionally be supported on carriers, for example on carbon or calcium carbonate. The hydrogenation can preferably be carried out at pressures of from 1 to approximately 100 atmospheres and at temperatures of from approximately −80° to approximately 200° C., especially at from room temperature to approximately 100° C. The reaction is advantageously carried out in a solvent, such as water, a lower alkanol, for example ethanol, iso propanol or n-butanol, an ether, for example dioxan, or a lower alkanecarboxylic acid, for example acetic acid.

Salts of compounds of the formula (I) having saltforming groups can be manufactured in a manner known per se. For example, salts of compounds of the formula (I) having acidic groups can be formed, for example, by treatment with metal compounds, such as alkali metal alcoholates or alkali metal salts of suitable organic carboxylic acids, for example the sodium salt of α-ethylcaproic acid, or with inorganic alkali metal or alkaline earth metal salts, for example sodium bicarbonate, or with ammonia or a suitable organic amine, there preferably being used stoichiometric amounts or only a small excess of the salt-forming agent.

Salts can be converted in customary manner into the free compounds, for example metal and ammonium salts can be converted into the free compounds by treatment with suitable acids.

The invention also relates to those embodiments of the process according to which compounds obtainable as intermediates at any stage of the process are used as starting materials and the remaining steps are carried out and/or a starting material is used in the form of a salt, isomer and/or racemate or antipode or, especially, is formed under the reaction conditions.

As a result of the close relationship between the novel compounds in free form and in the form of their salts, hereinbefore and hereinafter the free compounds or their salts shall be understood to mean optionally also the corresponding salts or free compounds, respectively, where appropriate with regard to meaning and purpose.

The novel compounds, including their salts, can also be obtained in the form of the hydrates or can include other solvents used for crystallisation.

Depending on the starting materials and methods chosen, the novel compounds may be in the form of one of the possible isomers or in the form of mixtures thereof, for example, depending on the number of asymmetrical carbon atoms, in the form of pure optical isomers, such as antipodes, or in the form of mixtures of isomers, such as racemates, mixtures of diastereoisomers or mixtures of racemates.

Resulting mixtures of diastereoisomers and mixtures of racemates can be separated on the basis of the physico-chemical differences between the constituents, in known manner, into the pure isomers, diastereoisomers or racemates, for example by chromatography and/or fractional crystallisation. Resulting racemates can furthermore be resolved into the optical antipodes by known methods, for example by recrystallisation from an optically active solvent, with the aid of microorganisms or by conversion into diastereoisomeric salts or esters, for example by reacting an acidic end product with an optically active base that forms salts with the racemic acid, or with an optically active carboxylic acid or a reactive derivative thereof, and separating the mixture of diastereoisomers obtained in this manner, for example on the basis of their different solubilities, into the diastereoisomers, from which the desired enantiomer can be freed by the action of suitable agents. Advantageously, the more active enantiomer is isolated.

In the process of the present invention it is preferable to use those starting materials which result in the compounds described at the beginning as being especially valuable. The invention relates also to novel starting materials, their use, for example as the active ingredients of medicaments, formulation processes and processes for their manufacture.

The pharmaceutical preparations according to the invention, which contain the compound according to the invention or pharmaceutically acceptable salts thereof, are for enteral, such as oral or rectal, and parenteral administration to and for inhalation by (a) warm-blooded animal(s), the pharmacological active ingredient being contained alone or together with a pharmaceutically acceptable carrier. The daily dose of the active ingredient depends on age and individual condition and on the method of administration.

The novel pharmaceutical preparations contain, for example, from approximately 10% to approximately 90%, preferably from approximately 20% to approximately 60%, active ingredient. Pharmaceutical preparations according to the invention are, for example, those in aerosol or spray form or in dosage unit forms, such as dragées, tablets, capsules or suppositories, also eye or nose drops and ampoules. Pharmaceutical preparations according to the invention for enteral or parenteral administration are, for example, those in dosage unit forms, such as dragées, tablets, capsules or suppositories, also ampoules. These are manufactured in a manner known per se, for example by means of conventional mixing, granulating, confectioning, dissolving or lyophilising processes. For example, pharmaceutical preparations for oral administration can be obtained by combining the active ingredient with solid carriers, optionally granulating a resulting mixture and processing the mixture or granulate, if desired or necessary after the addition of suitable adjuncts, to form tablets or dragée cores.

Suitable carriers are especially fillers, such as sugars, for example lactose, saccharose, mannitol or sorbitol, cellulose preparations and/or calcium phosphates, for example tricalcium phosphate or calcium biphosphate, also binders, such as starch pastes, using, for example, corn, wheat, rice or potato starch, gelatine, tragacanth, methylcellulose and/or polyvinylpyrrolidone, and/or, if desired, disintegrators, such as the above-mentioned starches, also carboxymethyl starch, cross-linked polyvinylpyrrolidone, agar, alginic acid or a salt thereof, such as sodium alginate. Adjuncts are especially flow-regulating agents and lubricants, for example silica, talc, stearic acid or salts thereof, such as magnesium stearate or calcium stearate, and/or polyethylene glycol. Dragée cores are provided with suitable coatings that are optionally resistant to gastric juices, there being used, inter alia, concentrated sugar solutions which may contain gum arabic, talc, polyvinylpyrrolidone, polyethylene glycol and/or titanium dioxide, or lacquer solutions in suitable organic solvents or solvent mixtures or, for the production of coatings that are resistant to gastric juices, solutions of suitable cellulose preparations, such as acetylcellulose phthalate or hydroxypropylmethylcellulose phthalate. Colourings or pigments can be added to the tablets or dragée coatings, for example for identification purposes or to indicate different doses of active ingredient.

Further orally administrable pharmaceutical preparations are dry-filled capsules consisting of gelatine and also soft, sealed capsules consisting of gelatine and a plasticiser, such as glycerine or sorbitol. The dry-filled capsules may contain the active ingredient in the form of a granulate, for example in admixture with fillers, such as lactose, binders, such as starches, and/or glidants, such as talc or magnesium stearate, and optionally stabilisers. In soft capsules, the active ingredient is preferably dissolved or suspended in suitable liquids, such as fatty oils, paraffin oil or liquid polyethylene glycols, it being possible also to add stabilisers.

As rectally administrable pharmaceutical preparations there come into consideration, for example, suppositories which consist of a combination of the active ingredient with a suppository base. Suitable suppository bases are, for example, natural or synthetic triglycerides, paraffin hydrocarbons, polyethylene glycols and higher alkanols. It is also possible to use gelatine rectal capsules which contain a combination of the active ingredient with a base material; as base materials there come into consideration, for example, liquid triglycerides, polyethylene glycols and paraffin hydrocarbons.

Especially suitable for parenteral administration are aqueous solutions of an active ingredient in water-soluble form, for example a water-soluble salt, also suspensions of the active ingredient, such as corresponding oily injection suspensions, there being used suitable lipophilic solvents or vehicles, such as fatty oils, for example sesame oil, or synthetic fatty acid esters, for example ethyl oleate or triglycerides, or aqueous injection suspensions that contain viscosity-increasing substances, for example sodium carboxymethylcellulose, sorbitol and/or dextran, and, optionally, stabilisers.

Inhalation preparations for the treatment of the respiratory system by nasal or buccal administration are, for example, aerosols or sprays which are able to disperse the pharmaceutical active ingredient in the form of a powder or in the form of drops of a solution or suspension. Preparations having powder-dispersing properties generally contain, in addition to the active ingredient, a liquid propellant gas having a boiling point below room temperature, and, if desired, carriers, such as liquid or solid, non-ionic or anionic surface-active agents and/or solid diluents. Preparations in which the pharmaceutical active ingredient is in solution contain, in addition to the active ingredient, a suitable propellant, and also, if necessary, an additional solvent and/or a stabiliser. It is also possible to use compressed air instead of the propellant gas.

The pharmaceutical inhalation preparations according to the invention are, for example, aerosol-forming mixtures, preferably mixtures forming solid aerosols, that is to say mixtures that can form inhalable aerosols, preferably inhalable solid aerosols, by means of their own vapour pressure or the pressure of a compressed gas, such as compressed air, laughing gas or carbon dioxide.

The invention relates also to the use of the novel compounds and their salts as pharmacologically active compounds, especially as anti-allergic agents, preferably in the form of pharmaceutical preparations, in a method for the treatment of allergic disorders. The dose administered, for example, to a warm-blooded animal weighing approximately 70 kg is, in the case of oral administration, from approximately 100 mg to approximately 1000 mg, preferably from approximately 250 mg to approximately 750 mg.

The following Examples illustrate the invention described above, but they are not intended to limit its scope in any way. Temperatures are given in degrees Centigrade.

EXAMPLE 1

2.94 g (0.024 mol) of oxalic acid monomethyl ester chloride are added to a solution of 5.05 g (0.0216 mol) of 3-amino-6-(n-butyl)-4H-1-benzothiopyran-4-one and 2.4 g (0.024 mol) of triethylamine in 325 ml of chloroform, the temperature of the reaction mixture rising to 30°. The mixture is then stirred for one hour at room temperature. The mixture is then concentrated to dryness by evaporation and the crystalline residue is stirred with ethanol, filtered with suction and washed first with ethanol and then with ether. After drying, N-[6-(n-butyl)-4H-1-benzothiopyran-4-on-3-yl]-oxalic acid amide methyl ester having a melting point of 192°–193.5° is obtained.

The starting material can be manufactured as follows:

143 g (0.86 mol) of P-(n-butyl)-thiophenol are added to a solution of 34.4 g (0.86 mol) of sodium hydroxide in 565 ml of water at approximately 20°. A further 131 ml of 2N sodium hydroxide solution are then added. A solution of 131.5 g (0.86 mol) of 3-bromopropionic acid in 334 ml of water and 52.4 g (0.49 mol) of anhydrous sodium carbonate is then added dropwise over a period of 30 minutes at a maximum of 30° and the reaction mixture is stirred at 40°–45° for 3 hours. After cooling, the mixture is extracted with ether. The aqueous phase is then poured into 300 ml of concentrated hydrochloric acid. The oil that separates out is taken up in methylene chloride, and the methylene chloride extract is dried with anhydrous magnesium sulphate and concentrated by evaporation and the residue that remains is stirred with a small quantity of petroleum ether. The mixture is left to stand in an ice bath for 3 hours and the crystalline product is then filtered off with suction. There is thus obtained 3-[4-(n-butyl)-phenylthio]-propionic acid having a melting point of 58°–59°.

129.2 g (0.542 mol) of 3-[4-(n-butyl)-phenylthio]-propionic acid are added in portions to 685 ml of concentrated sulphuric acid. The resulting solution is stirred at room temperature for 1 hour and then poured onto ice. The organic phase is then taken up in methylene chloride. The methylene chloride extract is washed once with water and once with 2N sodium hydroxide solution, dried with anhydrous magnesium sulphate and concentrated by evaporation. There is thus obtained 6-(n-butyl)-2,3-dihydro-4H-1-benzothiopyran-4-one in the form of a yellow oil.

A solution of 8.2 g (0.12 mol) of potassium hydroxide in 135 ml of ethanol is added dropwise at from 0° to 5° over a period of 45 minutes to a solution of 30.6 g (0.139 mol) of 6-(n-butyl)-2,3-dihydro-4H-1-benzothiopyran-4-one and 18 g (0.154 mol) of isopentyl nitrite in 85 ml of ethanol. The reaction mixture is then stirred at from 0° to 5° for 2 hours and then concentrated to dryness by evaporation. The potassium salt of 6-(n-butyl)-3-hydroxyimino-4H-1-benzothiopyran-4-one (oil) that remains is reacted further without purification.

60 ml of concentrated hydrochloric acid are added dropwise at approximately 20° over a period of 20 minutes to a solution of 56 g of crude potassium salt of 6-(n-butyl)-3-hydroxyimino-4H-1-benzothiopyran-4-one in 250 ml of glacial acetic acid. The reaction mixture is then stirred for 1 hour at from 0° to 5° and then concentrated to dryness by evaporation. The residue is stirred with methylene chloride and sodium hydroxide solution and the organic phase is separated off, washed twice with water and dried with anhydrous magnesium sulphate. Filtration is then carried out and the solution is concentrated to approximately 100 ml and filtered over a column filled with silica gel. Methylene chloride is used as eluant. The individual fractions, each of approximately 250 ml, are tested using thin-layer chromatography. Fractions 5 to 11 are combined, the solvent is distilled off and the oil that remains is triturated with petroleum ether and the product that crystallises out is filtered with suction. There is thus obtained 3-amino-2-chloro-6-(n-butyl)-4H-1-benzothiopyran-4-one having a melting point of 84.5°–86°.

A solution of 7.7 g (0.029 mol) of 3-amino-6-(n-butyl)-2-chloro-4H-1-benzothiopyran-4-one and 3.2 g of triethylamine in 160 ml of ethanol is hydrogenated at from 20° to 25° and normal pressure in the presence of 0.8 g of 10% palladium/carbon. The catalyst is filtered off and the filtrate is concentrated to dryness by evaporation; the residue is dissolved in methylene chloride and filtered over a column filled with silica gel, methylene chloride being used as eluant. From the main fractions there is obtained, after stirring with petroleum ether, pure 3-amino-6-(n-butyl)-4H-1-benzothiopyran-4-one having a melting point of 75°–76°.

EXAMPLE 2

6.15 g (0.0193 mol) of N-[6-(n-butyl)-4H-1-benzothiopyran-4-on-3-yl]-oxamide methyl ester are stirred with a solution of 22.6 ml of 1N sodium hydroxide solution in 147 ml of ethanol and 970 ml of water for 2 hours at 70°. A small degree of cloudiness is then removed by filtration and the filtrate is acidified with hydrochloric acid, a crystalline product being precipitated. After cooling, the crystals are filtered with suction and washed first with water, then with ethanol and subsequently with ether. After drying there is obtained N-[6-(n-butyl)-4H-1-benzothiopyran-4-on-3-yl)-oxalic acid monoamide having a melting point of 208° (decomposition).

EXAMPLE 3

In a manner analogous to that described in Example 1 it is possible to manufacture the following compounds:
N-(4H-1-benzothiopyran-4-on-3-yl)-oxamide methyl ester having a melting point of 260°,
N-(6-chloro-4H-1-benzothiopyran-4-on-3-yl)-oxamide methyl ester having a melting point of 305°, and
N-(6-methyl-4H-1-benzothiopyran-4-on-3-yl)-oxamide methyl ester having a melting point of 238°–240°.

EXAMPLE 4

In a manner analogous to that described in Example 1 it is possible to manufacture the following compounds:
N-(6,7-trimethylene-4H-1-benzothiopyran-4-on-3-yl)-oxamide methyl ester having a melting point of 255°–256°, and
N-(5,6-trimethylene-4H-1-benzothiopyran-4-on-3-yl)-oxamide methyl ester having a melting point of 265.5°–266.5°.

The starting material can be manufactured as follows:
In a manner analogous to that described in Example 1, starting from indan-5-thiol there is obtained 3-(3,4-trimethylenephenylthio)-propionic acid (brown oil) which, by treatment with concentrated sulphuric acid, yields an isomeric mixture. This consists predominantly of 6,7-trimethylene-2,3-dihydro-4H-1-benzothiopyran-4-one and also of 5,6-trimethylene- 2,3-dihydro-4H-1-benzothiopyran-4-one, melting point 61.5°–63.5°. This isomeric mixture is converted into an oxime with isopentyl nitrite and then treated with concentrated hydrochloric acid. After chromatography of the reaction products there are obtained 3-amino-2-chloro-6,7-trimethylene-4H-1-benzothiopyran-4-one having a melting point of 173°–174° and 3-amino-2-chloro-5,6-trimethylene-4H-1-benzothiopyran-4-one having a melting point of 133°–134°. Both isomers are hydrogenated in a manner analogous to that described in Example 1. There are thus obtained 3-amino-6,7-trimethylene-4H-1-benzothiopyran-4-one, melting point 145°–146°, and 3-amino-5,6-trimethylene-4H-1-benzothiopyran-4-one, melting point 172°–174°.

EXAMPLE 5

In a manner analogous to that described in Example 1 there is obtained:
N-(5,7-dimethyl-4H-1-benzothiopyran-4-on-3-yl)-oxamide methyl ester having a melting point of 208°–209°.

The starting material can be manufactured as follows:
In a manner analogous to that described in Example 1, starting from 3,5-dimethylthiophenol there is obtained 3-(3,5-dimethylphenylthio)-propionic acid, melting point 69°–70°, which is converted by way of 5,7-dimethyl-2,3-dihydro-4H-1-benzothiopyran-4-one, melting point 68°–69°, into the potassium salt of 3-hydroxyimino-5,7-dimethyl-3,4-dihydro-4H-1-benzothiopyran-4-one. This yields, after treatment with concentrated hydrochloric acid, 3-amino-2-chloro-5,7-dimethyl-4H-1-benzothiopyran-4-one, melting point 135.5°–136.5°, which, after hydrogenation, yields 3-amino-5,7-dimethyl-4H-1-benzothiopyran-4-one having a melting point of 117.5°–118.5°.

EXAMPLE 6

In a manner analogous to that described in Example 1 there is obtained:
N-(6-ethyl-4H-1-benzothiopyran-4-on-3-yl)-oxamide methyl ester having a melting point of 203.5°–205°.

The starting material can be manufactured as follows:
In a manner analogous to that described in Example 1, starting from 4-ethylthiophenol there is obtained 3-(4-ethylphenylthio)-propionic acid, melting point 59°–60°, which is converted into 6-ethyl-2,3-dihydro-4H-1-benzothiopyran-4-one (red oil). This is converted into an oxime with isopentyl nitrite, and the resulting crude potassium salt of 6-ethyl-3-hydroxyimino-2,3-dihydro-4H-1-benzothiopyran-4-one is converted with concentrated hydrochloric acid into 3-amino-2-chloro-6-ethyl-4H-1-benzothiopyran-4-one, melting point 79°–81°. After hydrogenation there is obtained 3-amino-6-ethyl-4H-1-benzothiopyran-4-one having a melting point of 106°–107°.

EXAMPLE 7

In a manner analogous to that described in Example 2 there are obtained:
N-(4H-1-benzothiopyran-4-on-3-yl)-oxalic acid monoamide having a melting point of 220° (decomposition),
N-(6-chloro-4H-1-benzothiopyran-4-on-3-yl)-oxalic acid monoamide having a melting point of 245° (decomposition),
N-(6-methyl-4H-1-benzothiopyran-4-on-3-yl)-oxalic acid monoamide having a melting point of 222° (decomposition),
N-(6,7-trimethylene-4H-1-benzothiopyran-4-on-3-yl)-oxalic acid monoamide monohydrate having a melting point of 223° (decomposition),
N-(5,6-trimethylene-4H-1-benzothiopyran-4-on-3-yl)-oxalic acid monoamide having a melting point of 225° (decomposition),
N-(5,7-dimethyl-4H-1-benzothiopyran-4-on-3-yl)-oxalic acid monoamide having a melting point of 217° (decomposition), and
N-(6-ethyl-4H-1-benzothiopyran-4-on-3-yl)-oxalic acid monoamide having a melting point of 196° (decomposition).

EXAMPLE 8

10 g (0.046 mol) of 3-amino-6,7-trimethylene-4H-1-benzothiopyran-4-one and 10.5 g (0.138 mol) of glycolic acid are heated at 120° for 1 hour. After cooling, the reaction mixture is stirred with water and the crystalline product is filtered off with suction, washed with water and dried. After recrystallisation from glacial acetic acid there is obtained pure N-(6,7-trimethylene-4H-1-benzothiopyran-4-on-3-yl)-2-hydroxyacetic acid monoamide having a melting point of 186.5°–188°. In an analogous manner there are obtained:
N-(4H-1-benzothiopyran-4-on-3-yl)-2-hydroxyacetic acid monoamide having a melting point of 159°–161°,
N-(6-chloro-4H-1-benzothiopyran-4-on-3-yl)-2-hydroxyacetic acid monoamide having a melting point of 215°–217°,
N-(6-methyl-4H-1-benzothiopyran-4-on-3-yl)-2-hydroxyacetic acid monoamide having a melting point of 222° (decomposition), and N-(5,6-trimethylene-4H-1-benzothiopyran-4-on-3-yl)-2-hydroxyacetic acid monoamide having a melting point of 225° (decomposition).

EXAMPLE 9

In a manner analogous to that described in Example 1 there are obtained:
starting from 3-amino-6,7-tetramethylene-4H-1-benzothiopyran-4-one,
N-(6,7-tetramethylene-4H-1-benzothiopyran-4-on-3-yl)-oxamide methyl ester having a melting point of 232°–233°, and
starting from 3-amino-5,6-tetramethylene-4H-1-benzothiopyran-4-one,
N-(5,6-tetramethylene-4H-1-benzothiopyran-4-on-3-yl)-oxamide methyl ester having a melting point of 246°–248°.

The starting material can be manufactured as follows:
By treating 3-(3,4-tetramethylenephenylthio)propionic acid [F. Krollpfeiffer and H. Schultze, Ber. 56, 1822 (1923)] with concentrated sulphuric acid there is obtained an oily isomeric mixture consisting of 6,7-tetramethylene-2,3-dihydro-4H-1-benzothiopyran-4-one and 5,6-tetramethylene-2,3-dihydro-4H-1-benzothiopyran-4-one. This isomeric mixture is converted into an oxime with isopentyl nitrite analogously to Example 1 and then treated with concentrated hydrochloric acid. After chromatography of the reaction product there are obtained 3-amino-2-chloro-6,7-tetramethylene-4H-1-benzothiopyran-4-one having a melting point of 175°–176°, and 3-amino-2-chloro-5,6-tetramethylene-4H-1-benzothiopyran-4-one having a melting point of 135.5°–136.5°. Both compounds are hydrogenated analogously to Example 1 to form 3-amino-6,7-tetramethylene-4H-1-benzothiopyran-4-one, melting point 147°–148°, and 3-amino-5,6-tetramethylene-4H-1-benzothiopyran-4-one, melting point 113°–114°.

EXAMPLE 10

In a manner analogous to that described in Example 2 there are obtained:
N-(6,7-tetramethylene-4H-1-benzothiopyran-4-on-3-yl)-oxalic acid monoamide hemihydrate having a melting point of 211° (decomposition), and
N-(5,6-tetramethylene-4H-1-benzothiopyran-4-on-3-yl)-oxalic acid monoamide having a melting point of 210–°211° (decomposition).

EXAMPLE 11

A solution of 9.2 g (0.048 mol) of m-chloroperbenzoic acid (90%) is added dropwise over a period of one hour to a solution of 6.4 g (0.02 mol) of N-[6-(n-butyl)-4H-1-benzothiopyran-4-on-3-yl]-oxamide methyl ester in 240 ml of chloroform. The reaction mixture is then stirred for 16 hours at room temperature, then extracted by shaking twice with 0.1N sodium bicarbonate solution, dried with anhydrous magnesium sulphate and concentrated to approximately 80 ml. This solution is filtered over a column filled with silica gel, methylene chloride being used as eluant. The individual fractions, each of approximately 300 ml, are monitored by thin-layer chromatography. Fractions 1 to 7 are combined, the solvent is distilled off and the residue that remains is stirred with ether and filtered with suction. The product so obtained is recrystallised from ethyl acetate. There is thus obtained pure N-[6-(n-butyl)-4H-1-benzothiopyran-1,1-dioxide-4-on-3-yl]-oxamide methyl ester having a melting point of 141.5° to 142.5°.

EXAMPLE 12

A solution of 3.03 g (0.0158 mol) of m-chloroperbenzoic acid (90%) is added dropwise over a period of 30 minutes to a solution of 5.05 g (0.0158 mol) of N-[6-(n-butyl)-4H-1-benzothiopyran-4-on-3-yl]-oxalic acid amide methyl ester in chloroform. The reaction mixture is stirred at room temperature for 22 hours, then concentrated to dryness by evaporation; the residue is dissolved in methylene chloride and the solution is filtered over a column filled with silica gel. Methylene chloride is used as eluant. The individual fractions, each of approximately 300 ml, are monitored by thin-layer chromatography. Fractions 9 to 15 are combined, the solvent is distilled off and the residue that remains is stirred with ether. There is thus obtained N-[6-(n-butyl)-1-oxido-4H-1-benzothiopyran-4-on-3-yl]-oxalic acid amide methyl ester having a melting point of 201°–202°.

EXAMPLE 13

5.25 g (0.02 mol) of N-(6-methyl-4H-1-benzothiopyran-4-on-3-yl)-oxalic acid monoamide are suspended in 40 ml of anhydrous dimethylformamide, and 2.66 g (0.022 mol) of tris-(hydroxymethyl)-aminomethane are added and the whole is heated to 70°. A clear solution is obtained. This solution is poured into 500 ml of acetone and the salt that crystallises out is filtered off with suction, washed with acetone and dried. There is thus obtained the tris-(hydroxymethyl)-aminomethane salt of N-(6-methyl-4H-1-benzothiopyran-4-on-3-yl)-oxalic acid monoamide, which is analytically pure and has a melting point of 198° (decomposition).

EXAMPLE 14

3.9 g (0.015 mol) of N-(6-methyl-4H-1-benzothiopyran-4-on-3-yl)-oxalic acid monoamide are suspended in 60 ml of anhydrous dimethylformamide, and 3.2 g (0.0164 mol) of N-methyl-D-glucamine are added and the whole is heated to 70°. A clear solution is obtained. On cooling, the salt crystallises out. 150 ml of acetone are added and the salt is filtered off with suction. The salt is then recrystallised from aoproximately 160 ml of methanol. There is thus obtained the N-methyl-D-glucamine salt of N-(6-methyl-4H-1-benzothiopyran-4-on-3-yl)-oxalic acid monoamide which is analytically pure and melts at 126° (decomposition).

EXAMPLE 15

In accordance with one of the procedures given in the description, in addition to the novel compounds mentioned in Examples 1 to 14 it is also possible to manufacture:
N-(2,6-dimethyl-4H-1-benzothiopyran-4-on-3-yl)-oxalic acid amide methyl ester,
N-(2,6-dimethyl-4H-1-benzothiopyran-4-on-3-yl)-oxalic acid monoamide,
N-(2-methyl-4H-1-benzothiopyran-4-on-3-yl)-oxalic acid monoamide, m.p. 195°,
N-(2-methyl-6,7-trimethylene-4H-1-benzothiopyran-4-on-3-yl)-oxalic acid monoamide,
N-(6-fluoro-4H-1-benzothiopyran-4-on-3-yl)-oxalic acid monoamide, m.p. 235° (decomposition), for example starting from 3-amino-6-fluoro-4H-1-benzothiopyran-4-one, m.p. 168°–169°,
N-(6-fluoro-4H-1-benzothiopyran-4-on-3-yl)-oxalic acid methyl ester, m.p. 294° (decomposition),
N-(6-methoxy-4H-1-benzothiopyran-4-on-3-yl)-oxalic acid methyl ester, m.p. 264°–266°, N-(6-methoxy-4H-1-benzothiopyran-4-on-3-yl)-oxalic acid monoamide, m.p. 234°, (decomposition), and N-(2-methyl-4H-1-benzothiopyran-4-on-3-yl)-oxalic acid amide methyl ester, m.p. 205°–207° (decomposition).

EXAMPLE 16

1.53 g (0,005 mol) of N-[6-(n-butyl)-4H-1-benzothiopyran-4-on-3-yl]-2-hydroxyacetic acid monoamide are dissolved in 60 ml of acetone and stirred with 1 g of potassium permanganate in 50 ml of water at room temperature for 48 hours. The reaction mixture is concentrated to dryness by evaporation under reduced pressure, and the residue is taken up in methylene chloride and washed with water. After drying the organic phase over sodium sulphate, it is concentrated. There is thus obtained N-[6-(n-butyl)-4H-1-benzothiopyran-4-on-3-yl]-oxalic acid monoamide having a melting point of 208° (decomposition).

EXAMPLE 17

0.3 g (0.0001 mol) of N-[6-(n-butyl)-4H-1-benzothiopyran-4-on-3-yl]-oxalic acid monoamide is dissolved in 20 ml of anhydrous methanol saturated with hydrochloric acid gas, and the whole is heated under reflux for 12 hours, cooled and concentrated to dryness by evaporation under reduced pressure. 10 ml of water are added to the residue and the whole is rendered alkaline with aqueous concentrated ammonia solution. Extraction is carried out twice with 20 ml of ethyl acetate, and the organic phase is washed at 5° with 10 ml of 2N potassium bicarbonate and 10 ml of water, dried over magnesium sulphate and concentrated to dryness under reduced pressure. There is thus obtained N-[6-(n-butyl)-4H-1-benzothiopyran-4-on-3-yl]-oxalic acid amide methyl ester having a melting point of 192°–193°.

EXAMPLE 18

1 g of N-[6-(n-butyl)-4H-1-benzothiopyran-4-on-3-yl]-trichloroacetamide is heated under reflux for 5 hours in 100 ml of ethanol and 10 ml of 25% sodium hydroxide solution. The solvent is removed in vacuo and the aqueous residue is acidified with 2N hydrochloric acid. There is thus obtained N-[6-(n-butyl)-4H-1-benzothiopyran-4-on-3-yl]-oxalic acid monoamide having a melting point of 208° (decomposition).

The starting material can be manufactured in a manner analogous to that described in Example 1 by reacting 3-amino-6-(n-butyl)-4H-1-benzothiopyran-4-one with trichloroacetyl chloride.

EXAMPLE 19

1.2 g (0.005 mol) of N-(4H-1-benzothiopyran-4-on-3-yl)-2-methoxyacetic acid monoamide are dissolved in 60 ml of acetone, and 25 ml of water are added. Potassium permanganate is then added in portions at room temperature while stirring vigorously until no further decoloration can be observed. The mixture is stirred for a further 12 hours and then filtered. The filtrate is concentrated to dryness at 50° and under reduced pressure. 20 ml of ice-water are added to the residue and the whole is taken up in chloroform. The organic phase is washed, dried over sodium sulphate and concentrated to dryness under reduced pressure. There is thus obtained N-(4H-1-benzothiopyran-4-on-3-yl)-oxalic acid amide methyl ester having a melting point of 192°–193°.

The starting material can be manufactured in a manner analogous to that described in Example 1 by reacting 3-amino-4H-1-benzothiopyran-4-one with 2-methoxyacetic acid.

EXAMPLE 20

6.1 g (0.025 mol) of N-[6-methyl-4H-1-benzothiopyran-4-on-3-yl]-cyanoformamide are dissolved in 75 ml of 90% sulphuric acid and the solution is stirred overnight at room temperature. The reaction mixture is then poured onto ice and the product that is formed is filtered off with suction. This product is washed first with water and then with ethanol. After drying there is obtained N-[6-methyl-4H-1-benzothiopyran-4-on-3-yl]-oxalic acid monoamide having a melting point of 222° (decomposition).

The N-[6-methyl-4H-1-benzothiopyran-4-on-3-yl]cyanoformamide can be manufactured, for example, from 3-amino-6-methyl-4H-1-benzothiopyran-4-one and cyanoformyl chloride [R. Appel et al., Angew. Chem. 95, (1983) 807].

EXAMPLE 21

2.4 g (0.01 mol) of N-[6-methyl-4H-1-benzothiopyran-4-on-3-yl]-cyanoformamide are suspended in 50 ml of methanol and heated at 80° for 14 hours (glass bomb tube). The reaction mixture is then extensively concentrated, filtered with suction and washed first with a small quantity of methanol and then with ether, and dried. There is thus obtained N-(6-methyl-4H-1-benzothiopyran-4-on-3-yl)-oxalic acid amide methyl ester having a melting point of 238°–240°.

EXAMPLE 22

9.6 g (0.05 mol) of 3-amino-6-methyl-4H-1-benzothiopyran-4-one, 0.52 g (0.005 mol) of oxalic acid monomethyl ester and 11.3 g (0.055 mol) of N,N'-dicyclohexyl carbodiimide are dissolved in 150 ml of tetrahydrofuran and the whole is stirred at room temperature for 6 hours. The reaction mixture is then concentrated to dryness by evaporation and the residue is stirred with 250 ml of methylene chloride; undissolved N,N'-dicyclohexylurea is filtered off with suction and the filtrate is concentrated and chromatographed over a column filled with silica gel. Methylene chloride is used as eluant and there is thus obtained N-(6-methyl-4H-1-benzothiopyran-4-on-3-yl)oxalic acid amide methyl ester having a melting point of 237°–239°.

EXAMPLE 23

5.5 g (0.02 mol) of N-(4H-2,3-dihydro-1-benzothiopyran-4-on-3-yl)-oxalic acid amide methyl ester are dissolved in a mixture of 80 ml of glacial acetic acid and 10 ml of acetic anhydride. 6.9 g (0.02 mol) of trityl perchlorate are then added at approximately 100°. The reaction mixture is then kept at 100° for a total of approximately 30 minutes, concentrated to dryness by evaporation under a water-jet vacuum and extracted with ether. The extraction residue is triturated with 150 ml of saturated sodium bicarbonate solution, filtered with suction, washed with water and dried. The crude product is then recrystallised from 2-ethoxyethanol. There is thus obtained N-(4H-1-benzothiopyran-4-on-3-yl)-oxalic acid amide methyl ester having a melting point of 258°.

The starting material can be manufactured as follows:
2.3 g (0.019 mol) of oxalic acid monomethyl ester chloride are added to a suspension of 3.7 g (0.017 mol) of 3-amino-2,3-dihydro-4H-1-benzothiopyran-4-one hydrochloride in 250 ml of chloroform, and then 3.8 g of triethylamine are added dropwise thereto. The reaction mixture is stirred for one hour at room temperature and then shaken twice with 100 ml of water each time, and the chloroform phase is dried with anhydrous magnesium sulphate and concentrated to dryness by evaporation. The oil that remains is dissolved in methylene chloride and chromatographed over a column filled with silica gel. There is thus obtained N-(4H-2,3-dihydro-1-benzothiopyran-4-on-3-yl)-oxalic acid amide methyl ester having a melting point of 107°-108°.

EXAMPLE 24

A solution of 8.9 g (0.025 mol) of N-[2-chloro-6-(n-butyl)-4H-1-benzothiopyran-4-on-3-yl]-oxalic acid amide methyl ester and 2.8 g of triethylamine in 200 ml of ethanol is hydrogenated at from 20° to 25° and at normal pressure in the presence of 1 g of 10% palladium/carbon. The catalyst is filtered off and the filtrate is concentrated to dryness by evaporation and the residue is recrystallised from 2-ethoxyethanol. There is thus obtained N-[6-(n-butyl)-4H-1-benzothiopyran-4-on-3-yl]-oxalic acid amide methyl ester having a melting point of 193°-195°.

The starting material, N-[2-chloro-6-(n-butyl)-4H-1-benzothiopyran-4-on-3-yl]-oxalic acid amide methyl ester can be obtained analogously to Example 1 by reacting 6.7 g (0.025 mol) of 2-chloro-3-amino-6-(n-butyl)-4H-1-benzothiopyran-4-one with 3.4 g (0.028 mol) of oxalic acid monomethyl ester chloride in the presence of 2.8 g (0.028 mol) of triethylamine.

EXAMPLE 25

A 2% aqueous solution, suitable for inhalation, of N-(6-methyl-4H-1-benzothiopyran-4-on-3-yl)-oxalic acid monoamide can be manufactured as follows:

| active ingredient | 2.000 g |
|---|---|
| disodium salt of ethylenediamine-tetraacetic acid (stabiliser) | 0.010 g |
| benzalkonium chloride (preservative) | 0.010 g |
| distilled water | ad 100 ml |

The active ingredient is dissolved in freshly distilled water and to this solution there are added the disodium salt of ethylenediaminetetraacetic acid and the benzalkonium chloride, which is a mixture of alkylmethylbenzylammonium chlorides in which alkyl contains from 8 to 18 carbon atoms. After the components have completely dissolved, the resulting solution is made up to a volume of 100 ml with water, introduced into containers and sealed in gas-tight manner.

EXAMPLE 26

Capsules, suitable for insufflation, containing 0.025 g of N-(6-methyl-4H-1-benzothiopyran-4-on-3-yl)-oxalic acid monoamide can be manufactured as follows:

| active ingredient | 25.00 g |
|---|---|
| lactose, ground | 25.00 g |

The active ingredient and the lactose (very finely ground) are thoroughly mixed with one another. The resulting powder is sieved and introduced in 0.05 g portions into gelatine capsules.

EXAMPLE 27

Tablets containing 100 mg of N-(6,7-trimethylene-4H-1-benzothiopyran-4-on-3-yl)-oxalic acid monoamide as active ingredient can be manufactured, for example, having the following composition:

| Composition | per tablet |
|---|---|
| active ingredient | 100 mg |
| lactose | 50 mg |
| wheat starch | 73 mg |
| colloidal silica | 13 mg |
| talc | 12 mg |
| magnesium stearate | 2 mg |
| | 250 mg |

Manufacture

The active ingredient is mixed with the lactose, a portion of the wheat starch and with the colloidal silica and the mixture is forced through a sieve. A further portion of the wheat starch is made into a paste with 5 times the amount of water on a water bath and the pulverulent mixture is kneaded with this paste until a slightly plastic mass is obtained. This mass is forced through a sieve of approximately 1 mm mesh width and dried, and the dry granulate is again forced through a sieve. The remainder of the wheat starch, the talc and the magnesium stearate are then admixed. The resulting tablet mixture is compressed to form tablets each weighing 250 mg and having (a) breaking notch(es).

EXAMPLE 28

In a manner analogous to that described in Examples 25 to 27, it is also possible to manufacture pharmaceutical preparations containing a different compound according to any one of Examples 1 to 24.

We claim:

1. A benzothiopyranone of the formula

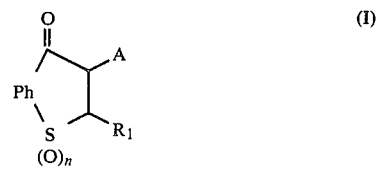

in which $R_1$ represents hydrogen, lower alkyl or lower alkenyl, n represents 0, 1 or 2, Ph represents 1,2-phenylene that is mono- or poly-substituted by lower alkyl, lower alkenyl, lower alkynyl, 3- or 4-membered lower alkylene briding two vicinal carbon atoms, hydroxy-lower alkyl, halo-lower alkyl, hydroxy, lower alkoxy, hydroxy-lower alkoxy, lower alkenyloxy, lower alkylthio, lower alkane-sulphinyl, lower alkanesulphonyl, lower alkanoyl, lower alkanoyloxy, nitro and/or by halogen or is unsubstituted, and A represents a group of the formula —NH—CO—R in which R represents carboxy, lower alkoxycarbonyl, or phenoxycarbonyl that is unsubstituted or mono- or poly-substituted by lower alkyl, lower alkenyl, lower alkynyl, 3- or 4-membered lower alkylene bridging two vicinal carbon atoms, hydroxy-lower alkyl, halo-lower alkyl, hydroxy, lower alkoxy, hydroxy-lower alkoxy, lower alkenyloxy, lower alkylthio, lower alkanesulphinyl, lower alkene-sulphonyl, lower alkanoyl, lower alkanoyloxy, nitro and/or by halogen, and a salt thereof.

2. A compound of claim 1 in which $R_1$ represents hydrogen or lower alkyl, n represents 0, 1 or 2, Ph represents 1,2-phenylene that is mono- or poly-substituted by lower alkyl, lower alkenyl, 3- or 4-membered lower alkylene bridging two vicinal carbon atoms, hydroxy-lower alkyl hydroxy, lower alkoxy, lower alkenyloxy, lower alkylthio, lower alkanesulphinyl, lowr alkanesulphonyl, lower alkanoyl, lower alkanoyloxy, nitro and/or by halogen or is unsubstituted, and A represents a group of the formula —NH—CO—R in which R represents carboxy or lower alkoxycarbonyl, and a salt thereof.

3. A compound of claim 1 in which $R_1$ represents hydrogen or lower alkyl, n represents 0, Ph represents 1,2-phenylene that is mono- or poly-substituted by lower alkyl, lower alkenyl, 3- or 4-membered lower alkylene bridging two vicinal carbon atoms, lower alkoxy and/or by halogen or is unsubstituted, and A represents a group of the formula —NH—CO—R in which R represents carboxy or lower alkoxycarbonyl, and a salt thereof.

4. A compound of claim 1 in which $R_1$ represents hydrogen, n represents 0, Ph represents 1,2-phenylene that is mono- or poly-substituted by lower alkyl, 3- or 4-membered lower alkylene bridging two vicinal carbon atoms and having from 3 up to and including 7 carbon atoms, lower alkoxy and/or by halogen or is unsubstituted, and A represents a group of the formula —NH—CO—R in which R represents carboxy or lower alkoxycarbonyl, and a salt thereof.

5. A compound of claim 1 of the formula

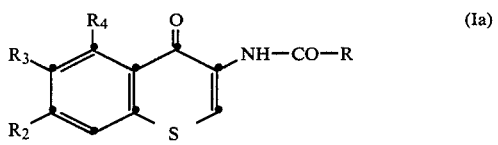
(Ia)

(a) in which R represents carboxy, $R_2$ and $R_4$ represent hydrogen and $R_3$ represents hydrogen, lower alkyl having up to and including 4 carbon atoms or lower alkoxy having up to and including 4 carbon atoms, or
(b) in which R represents carboxy, $R_2$ and $R_3$ together represent tri- or tetra-methylene and $R_4$ represents hydrogen, and a salt thereof.

6. A compound of claim 1 of the formula

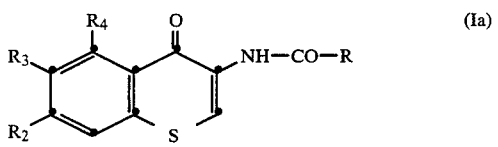
(Ia)

in which R represents carboxy, $R_2$ and $R_4$ represent hydrogen and $R_3$ represents lower alkyl having up to and including 4 carbon atoms, or $R_2$ and $R_3$ together represent tri- or tetra-methylene and $R_4$ represents hydrogen, or $R_3$ and $R_4$ together represent tri- or tetra-methylene and $R_2$ represents hydrogen, and a salt thereof.

7. A compound of claim 1 of the formula

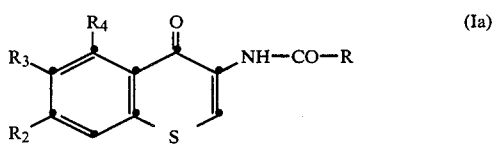
(Ia)

in which R represents carboxy, $R_2$ and $R_4$ represent hydrogen and $R_3$ represents lower alkyl having up to and including 4 carbon atoms, or in which $R_2$ and $R_3$ together represent tri- or tetra-methylene and $R_4$ represents hydrogen, and a salt thereof.

8. A compound of claim 7 wherein $R_3$ is methyl, or a salt thereof.

9. N-[6-(n-butyl)-4H-1-benzothiopyran-4-on-3-yl]-oxalic acid amide methyl ester, N-[6-(n-butyl)-4H-1-benzothiopyran-4-on-3-yl]-oxalic acid monoamide or a salt thereof, N-(4H-1-benzothiopyran-4-on-3-yl)-oxamide methyl ester, N-(6-chloro-4H-1-benzothiopyran-4-on-3-yl)-oxamide methyl ester, N-(6-methyl-4H-1-benzothiopyran-4-on-3-yl)-oxamide methyl ester, N-(6,7-trimethylene-4H-1-benzothiopyran-4-on-3-yl)-oxamide methyl ester, N-(5,6-trimethylene-4H-1-benzothiopyran-4-on-3-yl)-oxamide methyl ester, N-(5,7-dimethyl-4H-1-benzothiopyran-4-on-3-yl)-oxamide methyl ester, N-(6-ethyl-4H-1-benzothiopyran-4-on-3-yl)-oxamide methyl ester, N-(6-chloro-4H-1-benzothiopyran-4-on-3-yl)-oxalic acid monoamide or a salt thereof, N-(6,7-tetramethylene-4H-1-benzothiopyran-4-on-3-yl)-oxamide methyl ester, N-(5,6-tetramethylene-4H-1-benzothiopyran-4-on-3-yl)-oxamide methyl ester, N-[6-(n-butyl)-4H-1-benzothiopyran-1,1-dioxide-4-on-3-yl]-oxamide methyl ester, N-[6-(n-butyl)-1-oxido-4H-1-benzothiopyran-4-on-3-yl]]-oxalic acid amide methyl ester, N-(2,6-dimethyl-4H-1-benzothiopyran-4-on-3-yl)-oxalic acid amide methyl ester; N-(2,6-dimethyl-4H-1-benzothiopyran-4-on-3-yl)-oxalic acid monoamide or a salt thereof, N-(2-methyl-4H-1-benzothiopyran-4-on-3-yl)-oxalic acid monoamide or a salt thereof, N-(2-methyl-6,7-trimethylene-4H-1-benzothiopyran-4-on-3-yl)-oxalic acid monoamide or a salt thereof, N-(6-fluoro-4H-1-benzothiopyran-4-on-3-yl)-oxalic acid monoamide cr a salt thereof, N-(6-fluoro-4H-1-benzothiopyran-4-on-3-yl)-oxalic acid methyl ester, N-(6-methoxy-4H-1-benzothiopyran-4-on-3-yl)-oxalic acid methyl ester, or N-(6-methoxy-4H-1-benzothiopyran-4-on-3-yl)-oxalic acid monoamide or a salt thereof as claimed in claim 1.

10. N-(4H-1-benzothiopyran-4-on-3-yl)-oxalic acid monoamide or a salt thereof.

11. N-(6-methyl-4H-1-benzothiopyran-4-on-3-yl)-oxalic acid monoamide or a salt thereof.

12. N-(6,7-trimethylene-4H-1-benzothiopyran-4-on-3-yl)-oxalic acid monoamide or a salt thereof.

13. N-(5,6-trimethylene-4H-1-benzothiopyran-4-on-3-yl)-oxalic acid monoamide or a salt thereof.

14. N-(5,7-dimethyl-4H-1-benzothiopyran-4-on-3-yl)-oxalic acid monoamide or a salt thereof.

15. N-(6-ethyl-4H-1-benzothiopyran-4-on-3-yl)-oxalic acid monoamide or a salt thereof.

16. N-(6,7-tetramethylene-4H-1-benzothiopyran-4-on-3-yl)-oxalic acid monoamide or a salt thereof.

17. N-(5,6-tetramethylene-4H-1-benzothiopyran-4-on-3-yl)-oxalic acid monoamide or a salt thereof.

18. A pharmaceutical preparation comprising an antiallergically effective amount of a compound of claim 1, or a pharmaceutically acceptable salt thereof, in addition to a customary pharmaceutical adjunct or carrier.

19. A method for the treatment of allergic disorders in warmblooded organisms which comprises administering to such organism an antiallergically effective amount of a compound of formula I of claim 1 or a pharmaceutically acceptable salt thereof.

* * * * *